United States Patent
Evans et al.

(10) Patent No.: US 10,980,948 B2
(45) Date of Patent: Apr. 20, 2021

(54) LABELING APPARATUS FOR A MEDICAL DEVICE

(71) Applicant: West Pharmaceutical Services, Inc., Exton, PA (US)

(72) Inventors: Christopher Evans, Long Valley, NJ (US); Brian Costello, Whitehouse Station, NJ (US); Stacy Faught, Scottsdale, AZ (US)

(73) Assignee: WEST PHARMACEUTICAL SERVICES, INC., Exton, PA (US)

( * ) Notice: Subject to any disclaimer, the term of this patent is extended or adjusted under 35 U.S.C. 154(b) by 0 days.

(21) Appl. No.: 16/078,064

(22) PCT Filed: Feb. 22, 2017

(86) PCT No.: PCT/US2017/018967
§ 371 (c)(1),
(2) Date: Aug. 21, 2018

(87) PCT Pub. No.: WO2017/147198
PCT Pub. Date: Aug. 31, 2017

(65) Prior Publication Data
US 2019/0336692 A1    Nov. 7, 2019

Related U.S. Application Data

(60) Provisional application No. 62/298,238, filed on Feb. 22, 2016.

(51) Int. Cl.
*A61M 5/00* (2006.01)
*A61M 5/315* (2006.01)
(Continued)

(52) U.S. Cl.
CPC .......... *A61M 5/3157* (2013.01); *G01R 19/15* (2013.01); *G09F 3/0291* (2013.01);
(Continued)

(58) Field of Classification Search
CPC ...... A61M 2205/60; A61M 2205/6063; A61M 2205/6072; A61M 5/5086;
(Continued)

(56) References Cited

U.S. PATENT DOCUMENTS 2,612,994 A * 10/1952 Woodland .......... G06K 7/10871
                                                209/583
4,853,521 A *  8/1989 Claeys ................... G16H 20/17
                                                235/375
(Continued)

FOREIGN PATENT DOCUMENTS

DE      102010022701 A1    12/2011
EP          1402470 A1     3/2004
(Continued)

OTHER PUBLICATIONS

Int'l Search Report and Written Opinion in Int'l Application No. PCT/US17/18967 dated Jun. 12, 2017.
(Continued)

*Primary Examiner* — William R Carpenter
(74) *Attorney, Agent, or Firm* — Panitch Schwarze Belisario & Nadel LLP

(57) ABSTRACT

An apparatus for presenting an application status of a medical device that has a unused state and a used state. The apparatus includes a label having an electrochromic element. The label is at least partially disposed on an exterior surface of the medical device and is configured to display a predetermined feature in response to an electric current. A power source is disposed in or on the medical device for providing the electric current. A switch is configured to selectively connect or disconnect the label and the power source to one another for controlling the application of the electric current to the electrochromic element in response to actuation of the medical device from the unused state to the used state. The label may be scanned by a scan device that (Continued)

may connect to a medical organization for communicating information between the scan device and the medical organization.

13 Claims, 4 Drawing Sheets

(51) Int. Cl.
*G01R 19/15* (2006.01)
*G09F 3/00* (2006.01)
*A61B 90/00* (2016.01)
*A61J 1/00* (2006.01)
*A61M 5/20* (2006.01)
*A61M 5/31* (2006.01)

(52) U.S. Cl.
CPC .... *G09F 3/0297* (2013.01); *A61B 2090/0807* (2016.02); *A61J 1/00* (2013.01); *A61J 2205/30* (2013.01); *A61M 5/20* (2013.01); *A61M 2005/3126* (2013.01); *A61M 2205/0272* (2013.01); *A61M 2205/6063* (2013.01); *A61M 2207/10* (2013.01)

(58) Field of Classification Search
CPC .......... A61B 2090/0814; A61J 2205/30; G09F 3/0297; G09F 3/0291
See application file for complete search history.

(56) References Cited

U.S. PATENT DOCUMENTS

| | | | | |
|---|---|---|---|---|
| 5,258,789 A * | 11/1993 | Labaziewicz | ........ | G03B 17/30 396/207 |
| 5,700,998 A * | 12/1997 | Palti | ........ | G16H 20/13 235/375 |
| 5,737,114 A | 4/1998 | Bailey | | |
| 5,798,514 A * | 8/1998 | Domanik | ........ | G06K 19/06028 235/462.03 |
| 6,248,090 B1 * | 6/2001 | Jensen | ........ | A61M 5/31525 604/67 |
| 6,270,724 B1 * | 8/2001 | Woodaman | ........ | G01N 33/02 422/416 |
| 2001/0028308 A1 * | 10/2001 | De La Huerga | .. | A61M 5/14212 340/573.1 |
| 2002/0038392 A1 * | 3/2002 | De La Huerga | ....... | G16H 20/17 710/8 |
| 2002/0188259 A1 * | 12/2002 | Hickle | ........ | G06K 19/0723 604/189 |
| 2006/0118612 A1 * | 6/2006 | Christoffersen | ........ | A61J 1/06 235/375 |
| 2007/0056871 A1 * | 3/2007 | Griffiths | ........ | G09F 23/00 206/459.1 |
| 2008/0129960 A1 * | 6/2008 | Heacock | ........ | G01D 7/005 351/159.31 |
| 2009/0014539 A1 * | 1/2009 | Gelbman | ........ | G06F 3/1454 235/492 |
| 2009/0137957 A1 * | 5/2009 | Wagener | ........ | A61M 5/14276 604/151 |
| 2010/0160894 A1 * | 6/2010 | Julian | ........ | A61M 5/2033 604/506 |
| 2011/0257602 A1 * | 10/2011 | Watanabe | ........ | A61M 5/20 604/189 |
| 2012/0080029 A1 * | 4/2012 | Koerner | ........ | G09F 23/00 128/203.12 |
| 2012/0241525 A1 * | 9/2012 | Borges | ........ | G16H 20/17 235/494 |
| 2013/0150785 A1 * | 6/2013 | Heacock | ........ | G02C 7/02 604/111 |
| 2013/0269592 A1 * | 10/2013 | Heacock | ........ | A61B 90/92 116/206 |
| 2014/0243635 A1 * | 8/2014 | Arefieg | ........ | A61B 5/150503 600/365 |
| 2015/0187234 A1 * | 7/2015 | Atkinson | ........ | G06K 19/0717 40/5 |
| 2015/0343152 A1 * | 12/2015 | Butler | ........ | A61M 5/31551 604/207 |
| 2016/0243314 A1 * | 8/2016 | Rodiera Olive | ..... | A61B 5/4833 |
| 2016/0259913 A1 * | 9/2016 | Yu | ........ | G16H 50/20 |
| 2016/0263327 A1 * | 9/2016 | Radmer | ........ | G16H 20/10 |

FOREIGN PATENT DOCUMENTS

| | | |
|---|---|---|
| EP | 1608305 A1 | 12/2005 |
| EP | 1999691 A2 | 12/2008 |
| EP | 2275158 A2 | 1/2011 |

OTHER PUBLICATIONS

Int'l Preliminary Report on Patentability dated Aug. 28, 2018 in Int'l Application No. PCT/US2017/018967.

* cited by examiner

LABELING APPARATUS FOR A MEDICAL DEVICE

CROSS-REFERENCE TO RELATED APPLICATION

This application is a section 371 of International Application No. PCT/US17/18967, filed Feb. 22, 2017, which was published Aug. 31, 2017 under International Publication No. WO 2017/147198 A1, which claims the benefit of U.S. Provisional Application No. 62/298,238, filed Feb. 22, 2016, the disclosures of which are incorporated herein by reference.

Embodiments of the present disclosure relate to apparatuses and techniques for presenting a status of a medical device using a label with electrochromic material.

BACKGROUND OF THE INVENTION

An auto-injection device (or auto-injector) is a medical device designed to deliver a dose of a particular drug to a patient. Auto-injection devices are typically spring-loaded syringes that are easy to use and intended for self-administration of the dose by patients or by untrained personnel. In certain circumstances, the auto-injection devices are identified by labels to provide users with identifications and instructions for administering the medical devices. However, information presented on the labels generally does not change in order to reflect a real-time status of the medical device, e.g., a use of the medical device.

U.S. Pat. No. 5,737,114 discloses "a label for electrochemical cell employs an electrochromic material so that when the material is connected to power provided by the electrochemical cell, the material will undergo a visible change as a result of a chemical reaction." The label has an incorporated state-of-charge indicator for the electrochemical cell. The indicator includes an electrochromic material to form an electrically conductive electrochromic electrode. The electrochromic material will undergo a visible change as a result of current being supplied from the electrochemical cell. The indicator with the electrochromic material uses the electrical charge of the electrochemical cell to power the indicator. However, no currently-available labeling apparatus have been applied to medical devices.

Currently-available labeling solutions for medical devices lack an ability to automatically reflect statuses of the medical devices. The status of a medical device may confuse a patient or a doctor who uses the medical device. In addition, automatic administration applications may not be supported because the label is unable to provide status information of the medical device.

In view of the foregoing reasons, it may be desirable to have a labeling apparatus that can automatically visualize a feature to reflect a use of a medical device.

BRIEF SUMMARY OF THE DISCLOSURE

In accordance with a first aspect disclosed herein, there is set forth a labeling apparatus for presenting an application status of a medical device having a first, unused state and a second, used state. The apparatus includes a label having an electrochromic element, the label being at least partially disposed on an exterior surface of the medical device and being configured to display a predetermined feature in response to an electric current, a power source disposed in or on the medical device, and a switch configured to selectively connect or disconnect the label and the power source to one another for controlling the application of the electric current to the electrochromic element in response to actuation of the medical device from the first state to the second state. In an example embodiment of the disclosed labeling apparatus, the switch is operated by a component of the medical device that is movable when the medical device is actuated from the first state to the second state.

In another example embodiment of the disclosed labeling apparatus, the medical device is an injection device and the movable component is a plunger for administering liquid medicine into a patient's body. The injection device may be an auto-injection device, and wherein the plunger has a plurality of positions. The plurality of positions may comprise at least a fully plunged position and a non-fully plunged position. The switch may comprise a plurality of conductive members for connecting or disconnecting the power source and the label. At least one first conductive member selected from the conductive members may be attached to one of the power source and the label, and at least one second conductive member selected from the conductive members, other than the first conductive member, may be connected to the movable component. The first conductive member contacts the second conductive member when the plunger is moved to the fully plunged position during a normal course of injection for completing the connection between the power source and the label.

In another example embodiment of the disclosed labeling apparatus, the predetermined feature is a figure that is recognizable by a scan device. The scan device may include an application program configured to allow the scan device to scan the label. The power source may be a zinc-carbon battery, a alkaline battery, a nickel-cadmium battery, a lithium battery or a manganese dioxide battery. In accordance with a further aspect disclosed herein, there is set forth a system for administering a medical device that comprises: a labeling apparatus provided in accordance to any one of the previous embodiments of the disclosed labeling apparatus and a scan device for scanning the label of said labeling apparatus. The scan device may comprise an application program for scanning the label of the labeling apparatus.

In another example embodiment of the disclosed systems, the scan device may be configured to acquire use information of the medical device based on a scan result of the label. The use information comprises a device status, a product use, injection verification, a timestamp or a combination thereof. In another example embodiment of the disclosed systems, the scan device may be configured to present a message on the scan device in response to the scan result of the label. The scan device may also be configured to communicate with a medical organization. In another example embodiment of the disclosed systems, the scan device may be configured to transmit use information of the medical device to the medical organization. The scan device may be configured to present instructive information received from the medical organization.

BRIEF DESCRIPTION OF ACCOMPANYING DRAWINGS

The foregoing summary, as well as the following detailed description of preferred embodiments of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings.

It should be noted that the figures are not necessarily drawn to scale and that elements of familiar structures or functions are generally represented by like reference numerals for illustrative purpose throughout the figures.

DETAILED DESCRIPTION OF ASPECTS OF THE DISCLOSURE

Figure 1:
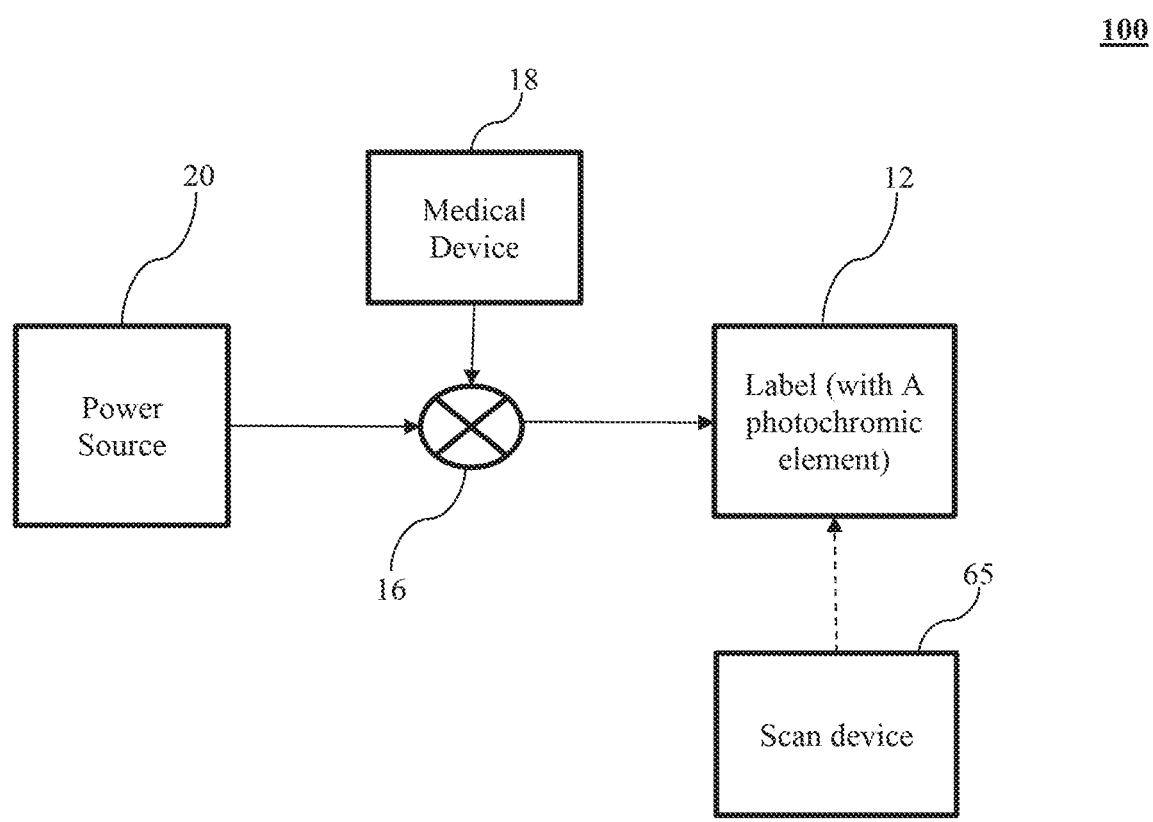
FIG. 1 is a conceptual block diagram of a labeling apparatus for presenting a status of a medical device according to an aspect of this disclosure.

Certain terminology is used in the following description for convenience only and is not limiting. The words "right," "left," "lower" and "upper" designate directions in the drawings to which the reference is made. The words "inwardly" and "outwardly" refer to directions toward and away from, respectively, the geometric center of the apparatus and designated parts thereof. The terminology includes the words above specifically mentioned, derivatives thereof and words of similar import.

Currently available medical devices, such as auto-injection devices, lack a satisfactory solution for indicating a status of a medical device according to use of the medical device. Accordingly, it is difficult to accurately track use of the medical devices and to guarantee adherence to application protocols. A label that can automatically reflect the use of the medical device may advantageously provide a desirable solution. This result may be achieved, according to one aspect of this disclosure, by an example labeling apparatus 100 illustrated in FIG. 1.

Turning to FIG. 1, the example labeling apparatus 100 may be enabled to reflect a status of a medical device 18 using a label 12. In FIG. 1, an electric power source 20 may be provided for applying an electric current, e.g., a small electric current in the milli-ampere range, to the label 12. The electric power source 20 may be a suitable type of battery, e.g., a watch battery or a button cell, including, but not limited to, zinc-carbon battery, alkaline battery, nickel-cadmium battery, lithium battery, manganese dioxide battery, and the like. The power source 20 is preferably sized so as to fit in or on the medical device 18.

The medical device 18 may be any type of device for medical purposes, including, but not limited to, an injection device, e.g., an auto-injection device (also known as auto-injector or auto-syringe, such as the ConfiDose® autoinjector, available from the Applicant), a surgical device, a medication container, or any other type of devices that are used for medical purpose. In some embodiments of this disclosure, the medical device 18 may have at least two statuses, e.g., an unused status and a used status. For example, the medical device 18 may include at least one movable element that may change a position relative to a main body of the medical device 18. Additional detail regarding the medical device 18 will be provided below with reference to FIG. 2A.

The medical device 18 may be associated with an electrical switch 16 that may control a connection between the power source 20 and the label 12. The switch 16 may be a suitable electrical component that may connect and/or break an electrical circuit. An example of the switch 16 will be set forth below with reference to FIG. 3A. According to some aspects of the disclosure, the switch 16 may be operated or controlled by standard use of the medical device 18. For example, when a movable element of the medical device 18 is operated to a certain position in the normal course of an injection or the like, the switch 16 may be connected and, thereby, an electrical circuit may be complete and an electric current be applied from the power source 20 to the label 12.

The label 12 may include at least one electrochromic element that may form certain features. The electrochromic element may be responsive to the electric current and be arranged such that before an electric current runs through the electrochromic element, the features may not be visible or is only barely visible. When the electric current runs through the electrochromic element, the features become visible or clearer. In some embodiments, the features may stay visible even when the electric current stops running. The features formed by the electrochromic element are preferably arranged to indicate a use status of the medical device 18. The features may be recognizable by a human-being and/or scannable by a scan device 65. Additional detail regarding the label 12 will be provided below with reference to FIGS. 2B and 2C.

According to some further aspects of the disclosure, the features of the label 12 may recognizable and/or scannable by a scan device 65. After the use (or application) of the medical device 18, the label 12 may be scanned by the scan device 65 to record and/or confirm a successful application of the medical device 18. The scan device 65 preferably includes at least an imager (i.e., a camera or other type of image sensor), a processor, and a wireless or wired communication module, and may be, for example, a mobile device including, but not limited to, a smartphone, a tablet computer, a handheld scan device, or the like. The use information acquired by the scan device 65 based on the features presented on the label 12 may be transmitted to a medical organization (not shown) for further purposes, including, but not limited to, recording and/or analyzing the use information, and/or providing further instruction based on the use information. Successful applications of the medical device 18 may be tracked and, thereby, a patient user's adherence to the application protocol of the medical device 18 may be enhanced.

Figure 2A:
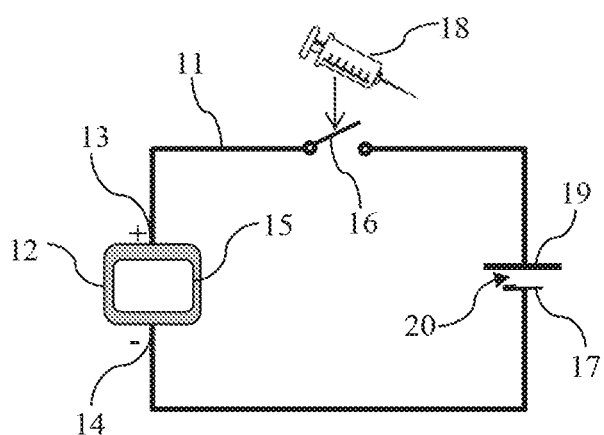
FIGS. 2A-2C are conceptual diagrams illustrating the labeling apparatus of FIG. 1, according to an aspect of this disclosure.

Turning to FIG. 2A, an example of the labeling apparatus 100 according to one aspect of this disclosure is illustrated in further detail. In FIG. 2A, the labeling apparatus 100 may include a label 12 having a display area 15. The display area 15 may include an electrochromic element (not shown) that can be arranged to form one or more visual features, e.g., a phrase "used" and/or a checkmark "✓". The label 12 may have two electro-terminals, one positive terminal 13 and one negative terminal 14. The electrochromic element may become light-absorbing when an electric current, runs through the two electro-terminals 13, 14. The visual features may remain visible after the current is cut off Additional detail regarding the label 12 will be provided below with reference to FIGS. 2B and 2C.

The negative terminal 14 of the label 12 may be connected to a negative electrode 17 (an anode) of a power source 20.

As shown and described herein, the power source 20 may be a suitable type of battery. The negative electrode 17 may be an anode of the battery 20 from which electrons flow out towards the circuit 11. The negative terminal 14 of the label 12 may be connected to the negative electrode 17 of the power source 20 directly or via an electrical switch (not shown).

The positive terminal 13 of the label 12 may be connected to a positive electrode 19 (or a cathode) of the power source 12 via a power switch 16. As shown and described herein, the switch 16 may be any type of circuit switch that can connect and/or break the circuit 11. As previously described above, the switch 16 may be operated and/or controlled by ordinary operation of the medical device 18. For example, the switch 16 may be switched on to connect the circuit 11 by a movement or a position of a movable component of the medical device 18. In one embodiment of this disclosure, when the medical device 18 is the auto-injection device, the switch 16 may be turned on when a piston (or plunger) (not shown in FIG. 2A) of the auto-injection device is in a predetermined position, e.g., a fully plunged position.

When the switch 16 is turned on, the circuit 11 may be completed. A current may run from the power source 20 to the circuit 11 and to the label 12, which may cause the electrochromic element of the label 12 to activate. The electrochromic element may visualize the visual features that may be recognizable by the scan device 56 (shown in FIG. 1).

Although shown and described as separated components for purposes of illustration only, the labeling apparatus 100, including the label 12, the power source 20, the circuit 11 and the switch 16, may be integrated into the medical device 18. Although shown and described as being provided to control the connection between the positive terminal 13 of the label 12 and the positive electrode 19 of the battery 20 for purposes of illustration only, the switch 16 may be provided to control the connection between the negative terminal 14 and the negative electrode 17.

Additionally and/or alternatively, although only including one label 12, one battery 20 and one switch 16 in the circuit 11 for illustration only, the circuit 11 may include additional electrical components (not shown) provided the additional electrical elements do not change a principle idea of this disclosure. The additional electrical components may be connected with the battery 20 and/or the label 12 via series or parallel connections and may include, but are not limited to, one or more resistors, capacitors, inducers, or the like for controlling a level of the electric current running through the label 12. Additionally and/or alternatively, according to some aspects of this disclosure, multiple batteries 20, labels 12, and or switches 16 can also be used.

Figures 2B, 2C:
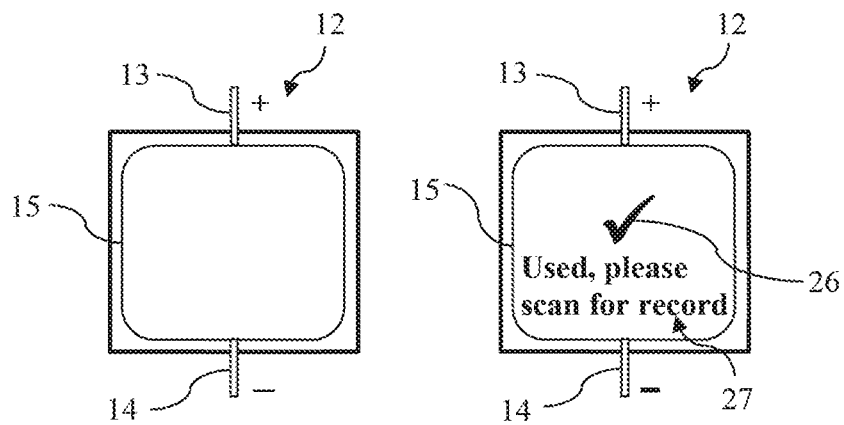

FIGS. 2B and 2C illustrate an example of the label 12. For example, the label 12 before application or use of the medical device 18 is shown in FIG. 2B, and the label 12 after the application or use of the medical device 18 is shown in FIG. 2C. In FIGS. 2B and 2C, the label 12 is shown as having a square shape and a display area 15 that may be at least partially arranged with at least one electrochromic element. The electrochromic element may consist of an electrochromic material and be arranged in accordance to one or more specific predetermined features, including, but not limited to, figures, codes (including machine readable codes, such as bar codes or the like), and/or phrases. As shown in FIG. 2C, the features may include a check mark "✓" and/or phrases to instruct a user of the medical device 18 what to do next. The features may be invisible or less visible before an electric current runs through the label 12 to activate the electrochromic material, as shown in FIG. 2B. The electrochromic material may have a light-absorbing property when activated by an electric current.

As shown and described with reference to FIG. 2A, the label 12 may include a positive terminal 13 and a negative terminal 14 for controllably connecting to the power source 20. Although shown and described as having two terminals 13, 14 for purposes of illustration only, the label 12 may be connected to the power source 20 via any type and/or number of connectors and may be connected via any suitable connection means.

As shown in FIG. 2C, for example, when the electric current runs through the label 12, the features defined by the electrochromic material may become visible. As set forth herein, one or more figures 26 and/or one or more phrases 27 may be arranged with the electrochromic material. Thereby, the user of the medical device 18 may be instructed by the phrases 27, and the figure 26 may be scanned by the scan device 65 (shown in FIG. 5, for example).

Although shown and described as the figure 26 and the phrases 27 for purposes of illustration only, the features may include any suitable type of features, e.g., an image, a diagram, a symbol, a code, a sign, a signal or any combination thereof.

Figure 3A:
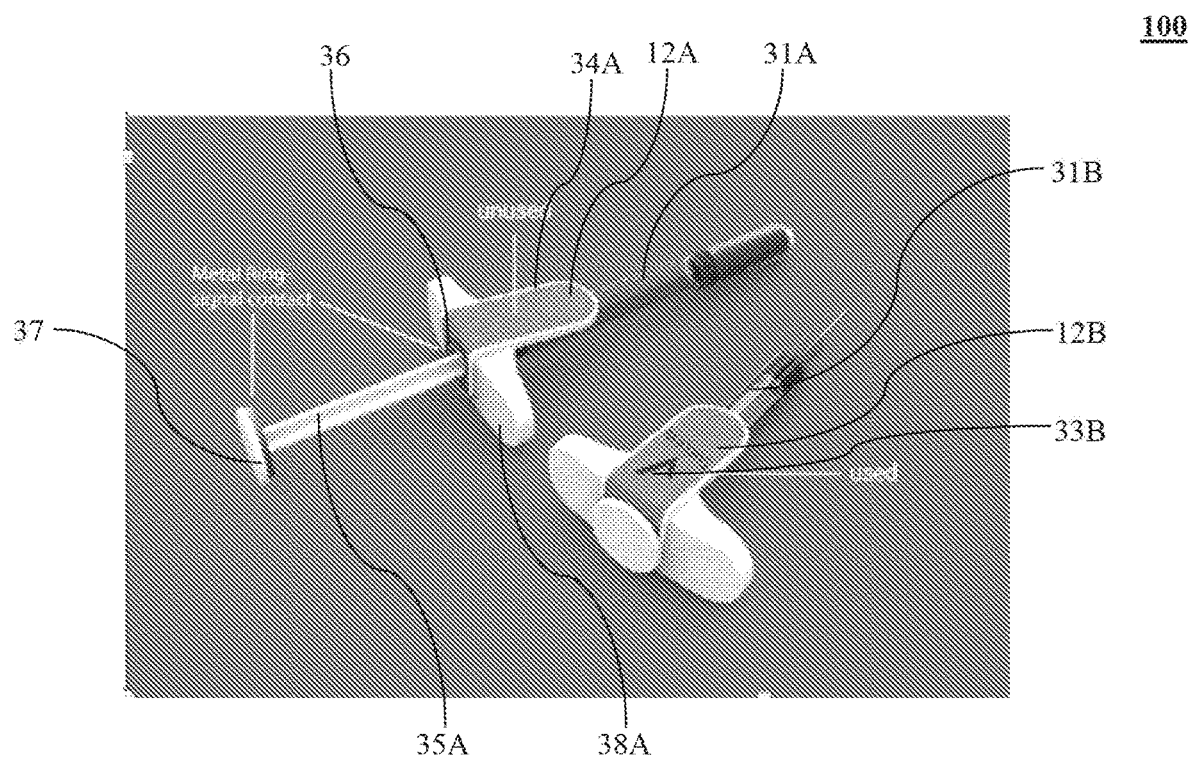
FIGS. 3A-3B are top side perspective views of exemplary medical devices in used and unused states with the labeling apparatus of FIG. 1, according to an aspect of this disclosure.

FIG. 3A illustrates an example of the labeling apparatus 100. Turning to FIG. 3A, two injection devices 31A, 31B are shown as the medical device 18 (FIG. 2). In FIG. 3A, the unused injection device 31A may include a label plate 34A that may consist of a label 12A. The label 12A may be visibly blank before the injection device 31A is applied. The label plate 34A may be a plate of an elongated shape, e.g., a square shape, a rectangle shape, a polygon or the like and may be made into a flat-shape or an L-shape. The label plate 34A may be made of any suitable material, e.g., a plastic or a metal material, and be attached to the injection device 31A.

The label 12A may include an electrochromic element and have two terminals 13, 14 for connecting the electrochromic element with a power source 20 via a circuit 11 (collectively shown in FIG. 2). The terminals 13, 14, the power source 20 and the circuit 11 may be hidden within the label plate 34A and/or a finger flange 38A (or top collar). The finger flange 38A may be a flange designed for index and middle fingers to hold the syringe while a plunger 35A of the injection device 31A is pushed. The injection device 31A may administer liquid medicine into a patient's body (not shown) by pushing the plunger 35A toward the finger flange 38A.

The terminals 13, 14 of the label 12A may be connected to the power source 20 via a switch 16 (shown in FIG. 4) formed by two conductive members 36, 37, e.g., ring-shaped metal members. A first conductive member 36 may be arranged, e.g., at a proximal position of the label 12A or the finger flange 38A and may consist of two separated elements 36A, 36B, each being connected to the circuit 11 (collectively shown in FIG. 4). A second conductive member 37 may be arranged at a distal end of the plunger 35A. The plunger 35A may have a plurality of predetermined positions. The switch 16 may be turned on to make the circuit 11 conductively complete when the plunger 35A reaches a selected predetermined position, e.g., a fully plunged position, as demonstrated by the other injection device 31B in FIG. 3A, where the second conductive member 37 may make contact with the first conductive member 36.

Figure 4:
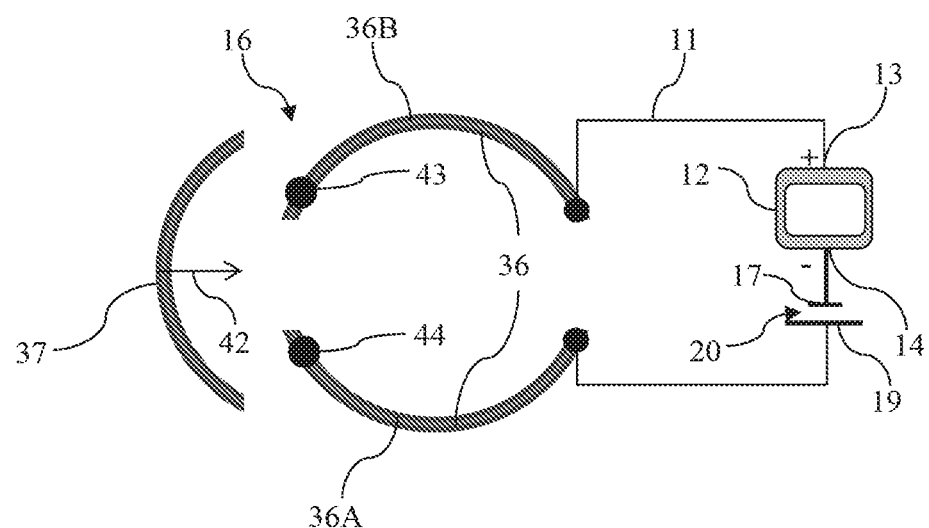
FIG. 4 is a conceptual diagram of an example of the labeling apparatus of FIGS. 3A-3B, according to an aspect of this disclosure.

Additional detail regarding the switch 16 and/or the first and second conductive members 36, 37 will be provided with reference to FIG. 4. When the switch 16 is connected, an electric current may run in the circuit 11 from the power source 20 to the label 12A. According to some aspects of the disclosure, the electric current may be a small electric current suitable to activate the electrochromic material contained in the label 12A.

When the electric current flows through the label 12A, the electrochromic material contained in the label 12A and arranged in forms of visual features may be made visible. The unused injection device 31A may become a used injection device 31B. The label 12A may be changed to label 12B, where a checkmark "✓" 33B and a phrase "success" may appear on the label 12B. The checkmark 33B and phrase "success" may not be faded or changed even when the electric current stops running in the circuit 11. Thus, through normal injection operation of the plunger 35A, the label 12B is activated to automatically signal use of the device 31B.

Although shown and described as the injection device 31A, 31B for purposes of illustration only, the labeling apparatus 100 may be used in any suitable medical device 18, including, but not limited to, a surgical device, a medication device, or any other type of devices that are used for medical purposes.

Figure 3B:
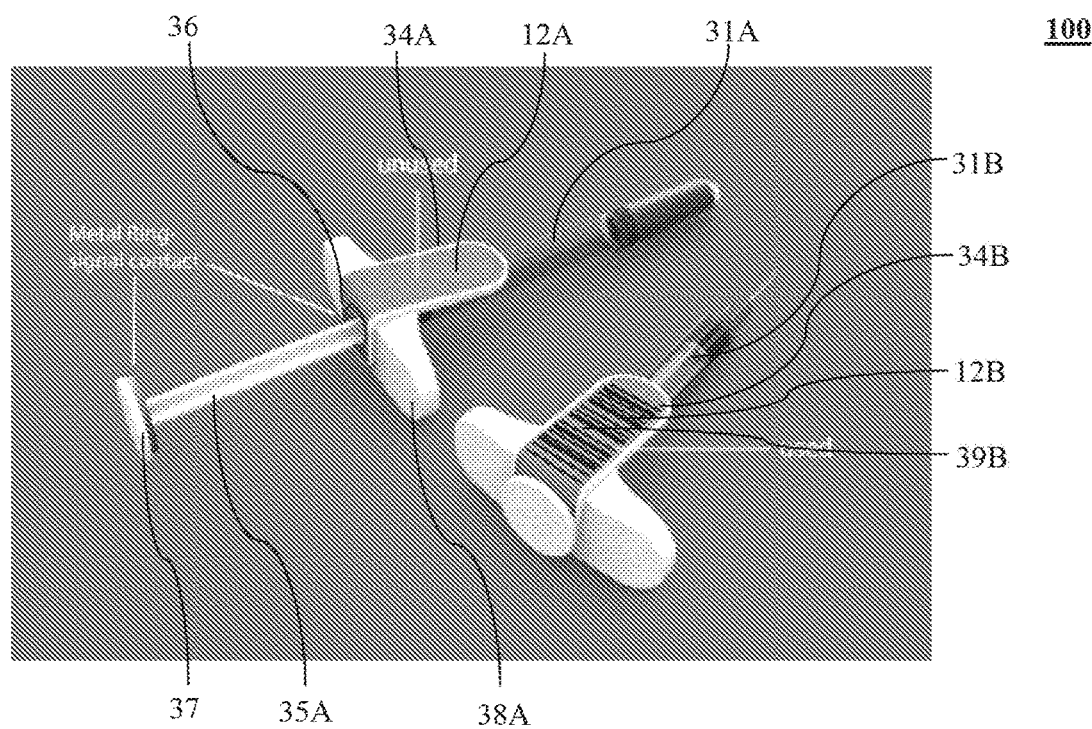

FIG. 3B illustrates a further example of the labeling apparatus 100. Turning to FIG. 3B, two injection devices 31A, 31B are shown as the medical device 18 (FIG. 2). In FIG. 3B, the label 12A may be configured to carry certain information of the medical device 18, e.g., the injection devices 31A, 31B. According to some aspects of the disclosure, the electrochromic material may be prearranged into certain feature pattern, including, but not limited to, a barcode pattern or a quick response code pattern.

When the injection device 31A is engaged by pushing the plunger 35A to a fully plunged position, the switch 16, consisting of two conductive members 36, 37, may be turned on (or connected) to complete the circuit 11 (collectively shown in FIG. 4). The electrodes of the power source 20 may be connected to respective terminals 13, 14 (collectively shown in FIG. 4) of the label 12A. An electric current may run through the electrochromic material arranged in the label 12A, which activate a light-absorbing property of the electrochromic material. Thereby, the prearranged feature pattern, a barcode 39B, defined by the electrochromic material may become visible. The unused injection device 31A may become a used injection device 31B. The label 12A may be changed to label 12B to indicate that the medical device 18 had been used and/or a medicine contained in the medical device 18 has been applied.

Figure 5:
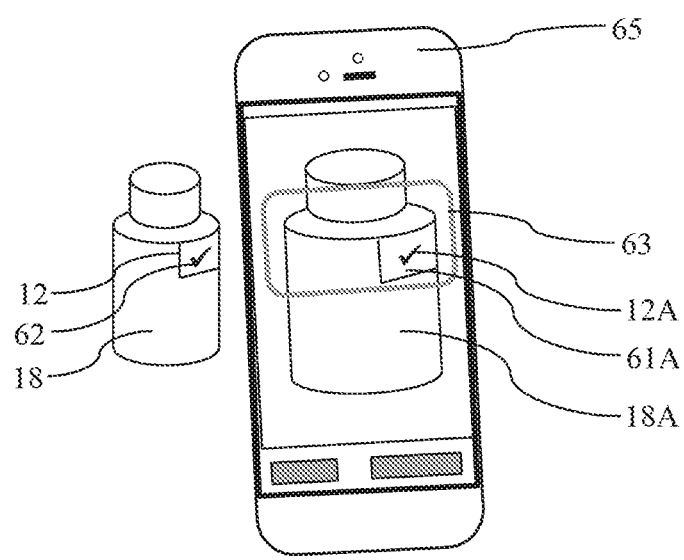
FIG. 5 is a conceptual diagram illustrating scanning of the label of the labeling apparatus of FIG. 1, according to an aspect of this disclosure.

The barcode 39B may be scannable by the scan device 65 (shown in FIG. 5). Additional detail regarding scanning the label 12B will be provided with reference to FIG. 5. Although shown and described as the barcode 39B or the quick response code for purposes of illustration only, any other types of features may be included in this disclosure as can be appreciated by a person skilled in the art, such as, an image, a picture, a signal, or the like.

FIG. 4 shows an example of the labeling apparatus 100 of FIGS. 3A and 3B. Turning to FIG. 4, details of the switch 16 of the labeling apparatus 100 are illustrated. In FIG. 4, a negative electrode 17 of a power source 20 may be connected to a negative terminal 14 of a label 12A via a circuit 11.

A positive electrode 19 of the power source 20 may be connected to a first element 36A of a first conductive member 36. A positive terminal 13 of the label 12 may be connected to a second element 36B of the first conductive member 36. The first element 36A may be separated from the second element 36B, thereby, the circuit 11 may be incomplete and no current may run from the power source 20 to the label 12.

A second conductive member 37 may be arranged to connect the first element 36A with the second element 36B when contacted with the first conductive member 36. As shown and described with reference to FIG. 3A, when the plunger 35A of the injection device 31A is pushed toward the finger flange 38A, the second conductive member 37 may move in a direction 42 towards the first conductive member 36. When the plunger 35A is in the fully plunged position, the second conductive member 37 may make contact with the first conductive member 36. According to some aspects of the disclosure, two contacts 43, 44 may be provided on each element 36A, 36B of the first conductive member 36 for ensuring a good electrical connection between the first conductive member 36 and the second conductive member 37. In some embodiments, contacts may be provided on the second conductive member 37 or both the first conductive member 36 and the second conductive member 37.

When the second conductive member 37 contacts the first conductive member 36, the first element 36A and the second element 36B of the first conductive member 36 may be connected to complete the circuit 11. An electric current may be run from the power source 20 to the label 12, thereby, activating the electrochromic material contained in the label 12 and making any features defined by the electrochromic material visible.

FIG. 5 illustrates an example of use of the labeling apparatus 100. Turning to FIG. 6, the label 12 may be scanned by the scan device 65 to account for the medical device 18 being used in accordance with an application protocol. The scan device 65 may have a screen to display a scanned object and may be installed with an application program ("app") that may recognize a visual feature 62 of the label 12 according to a predetermined protocol, e.g., the application protocol of the medical device 18.

Additionally and/or alternatively, the app may present a user (not shown) certain information regarding a use of the medical device 18 and, thereby, enhance an adherence to the application protocol by the user who may be a patient. The user may be instructed to scan the label 12 to account for the application of the medical device 18 at a certain time, e.g., after the application of the medical device 18. When the app is started on the scan device 65, a scan rectangle 63 may be displayed on the scan device 65 for defining a scan area in order to facilitate the user to point the scan device 65 to the label 12. When the scan device 65 is appropriately pointed to the label 12 of the medical device 18, the label 12 and the medical device 18 may be displayed as a label image 12A and medical device image 18A on the screen of the scan device 65. The label 12, including the visual feature 62, may be enclosed in the scan area 68. The visual feature 62 may be presented as a feature image 62A and be recognized in accordance to the predetermined protocol.

If the label 12 is scanned after the medical device 18 is applied, a confirmation message (not shown) may be presented on the screen of the scan device 65. For example, the confirmation message may say "the medical device is successfully applied." If the label 12 is scanned before the medical device 18 is applied or when the medical device 18 has not been applied in accordance to the application protocol, a warning message (not shown) may be presented on the screen of the scan device 65. The message may say "the medical device is not successfully applied. Please scan the label after a successful application of the medical device."

According to some other aspects of the disclosure, the app and/or the scan device 65 may transmit use information of the medical device 18 to a medical organization (not shown).

The use information may be any information that may be acquired based on a scanned information by the scan device 65. The medical organization may record a device status, product use, injection verification, timestamps and other milestones data, that may be acquired based on the use information. The use information may be transmitted to the medical organization via, e.g., a Bluetooth connection, a Wi-Fi connection, a ZigBee connection or any other suitable wired or wireless connections. The medical organization may acknowledge receipt of the use information and/or send reply information back to the scan device 65, which may be displayed on the screen of the scan device 65 for the user's attention.

Various aspects of the disclosure have been presented above. However, the invention is not intended to be limited to the specific aspects presented above, which have been presented for purposes of illustration. Rather, the invention extends to functional equivalents as would be within the scope of the appended claims. Those skilled in the art, having the benefit of the teachings of this specification, may make numerous modifications without departing from the scope and spirit of the invention in its various aspects.

What is claimed is:

1. An assembly comprising:
    an injection device having a first, unused state and a second, used state and comprising a syringe for administering liquid medicine into a patient's body, and
    a labeling apparatus for presenting an application status of the injection device comprising:
        a label having an electrochromic element, the label being at least partially disposed on an exterior surface of the injection device and being configured to display a predetermined feature in response to an electric current when the injection device is in the second, used state, the predetermined feature including a machine-readable code selected from the group consisting of a linear bar code and a quick response code;
        a power source disposed in or on the injection device; and
        a switch configured to selectively connect or disconnect the label and the power source to one another for controlling the application of the electric current to the electrochromic element in response to actuation of the injection device from the first state to the second state, the switch comprising a plurality of conductive members for connecting or disconnecting the power source and the label,
    wherein the switch is operated by a plunger of the injection device that is movable when the injection device is actuated from the first state to the second state, and
    wherein at least one first conductive member selected from the plurality of conductive members is electrically connected to one of the label or the power source, and at least one second conductive member selected from the plurality of conductive members, other than the first conductive member, is connected to the plunger.

2. The assembly of claim 1, wherein the plunger has a plurality of positions.

3. The assembly of claim 2, wherein the plurality of positions comprises at least a fully plunged position and a non-fully plunged position.

4. The assembly of claim 1, wherein the first conductive member contacts the second conductive member when the plunger is moved to the fully plunged position during a normal course of injection for completing the connection between the power source and the label.

5. The assembly of claim 1, wherein the power source is a zinc-carbon battery, a alkaline battery, a nickel-cadmium battery, a lithium battery or a manganese dioxide battery.

6. A system for administering an injection device, comprising:
    an assembly in accordance to claim 1; and
    a scan device for scanning the label.

7. The system of claim 6, wherein the scan device comprises an application program for scanning the label.

8. The system of claim 6, wherein the scan device is configured to acquire use information of the injection device based on a scan result of the label.

9. The system of claim 8, wherein the use information comprises a device status, a product use, injection verification, a timestamp or a combination thereof.

10. The system of claim 6, wherein the scan device is configured to present a message on the scan device in response to the scan result of the label.

11. The system of claim 10, wherein the scan device is configured to communicate with a medical organization.

12. The system of claim 11, wherein the scan device is configured to transmit use information of the injection device to the medical organization.

13. The system of claim 11, wherein the scan device is configured to present instructive information received from the medical organization.

* * * * *